United States Patent [19]

Sprecker et al.

[11] Patent Number: 4,902,672
[45] Date of Patent: Feb. 20, 1990

[54] POLYALKYL INDANYL N-PROPYL AND ALLYL ETHERS AND PERFUMERY USES THEREOF

[75] Inventors: Mark A. Sprecker, Sea Bright; Robert P. Belko, Woodbridge; Ronald S. Fenn, Bridgewater, all of N.J.

[73] Assignee: International Flavors & Fragrances Inc., New York, N.Y.

[21] Appl. No.: 371,294

[22] Filed: Jun. 26, 1989

[51] Int. Cl.$^4$ ................................................ A61K 7/46
[52] U.S. Cl. ........................................ 512/19; 568/665
[58] Field of Search ........................... 568/665; 512/19

[56] References Cited

U.S. PATENT DOCUMENTS

| | | | |
|---|---|---|---|
| 3,636,165 | 1/1972 | Hall | 260/617 F |
| 3,703,479 | 11/1972 | Theimer | 568/665 |
| 4,782,192 | 11/1988 | Light et al. | 568/665 |

*Primary Examiner*—James H. Reamer
*Attorney, Agent, or Firm*—Arthur L. Lieberman

[57] ABSTRACT

Described are polyalkyl indanyl n-propyl and allyl ethers defined according to the structure:

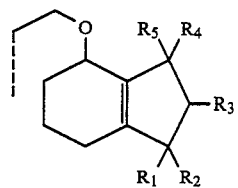

wherein $R_3$ represents methyl or hydrogen; wherein $R_1$, $R_2$, $R_4$ and $R_5$ each represents methyl or ethyl and wherein the dashed line represents a carbon-carbon single bond or a carbon-carbon double bond with the provisos that:

1. at least three of $R_1$, $R_2$, $R_4$ and $R_5$ represents methyl;
2. when each of $R_1$, $R_2$, $R_4$ and $R_5$ is methyl, then $R_3$ is methyl; and
3. when the dashed line is a carbon-carbon double bond and $R_1$, $R_2$, $R_3$, $R_4$ and $R_5$ are each methyl and uses thereof in augmenting or enhancing the aroma of perfume compositions, colognes and perfumed articles including but not limited to perfumed polymers, solid or liquid anionic, cationic, nonionic or zwitterionic detergents, fabric softener compositions, fabric softener articles, cosmetic powders and hair preparations.

4 Claims, 5 Drawing Sheets

GLC PROFILE FOR BULKED DISTILLATION FRACTIONS 20-31, EXAMPLE I.

FIG. 4  NMR SPECTRUM FOR EXAMPLE II.

POLYALKYL INDANYL N-PROPYL AND ALLYL ETHERS AND PERFUMERY USES THEREOF

BACKGROUND OF THE INVENTION

This invention relates to polyalkyl indanyl n-propyl and allyl ethers having the generic structure:

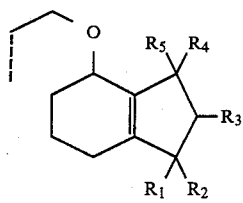

wherein the dashed line represents a carbon-carbon single bond or a carbon-carbon double bond; wherein $R_3$ represents methyl or hydrogen; wherein $R_1$, $R_2$, $R_4$ and $R_5$ each represents methyl or ethyl with the provisos that:
  1. at least three of $R_1$, $R_2$, $R_4$ and $R_5$ is methyl;
  2. when each of $R_1$, $R_2$, $R_4$ and $R_5$ is methyl, then $R_3$ is methyl; and
  3. when the dashed line is a carbon-carbon double bond then $R_1$, $R_2$, $R_3$, $R_4$ and $R_5$ are each methyl and uses thereof in augmenting or enhancing the aroma of perfume compositions, colognes and perfumed articles.

Materials which can provide musky, cigar box-like, amber, woody, patchouli and camphoraceous aromas with woody, winey and balsamic topnotes are highly desirable in the art of perfumery. Many of the natural substances which provide such fragrance nuances and contribute the desired nuances to perfumery compositions are high in cost, vary in quality from one batch to another and/or are generally subject to the usual variations of natural products.

The prior art contains a teaching regarding the use of tetrahydro pentylmethyl indane derivatives defined according to the structure:

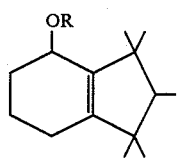

wherein R represents alkyl, acyl or hydrogen in perfumery. Thus, U.S. Pat. No. 3,636,165 issued on January 18, 1972 discloses the use of the genus having the structure:

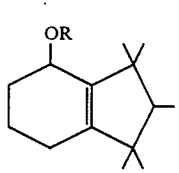

in perfumery and the species of that genus having the structure:

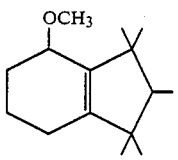

Such ethers are indicated to have "woody, balsamic" odors. The specification of U.S. Pat. No. 3,636,165 is incorporated herein by reference.

The compounds having the structures:

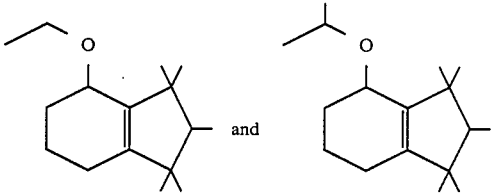

were prepared and compared with the compounds having the structures:

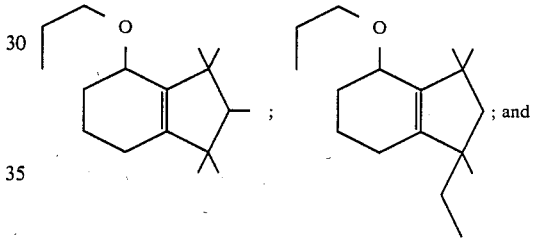

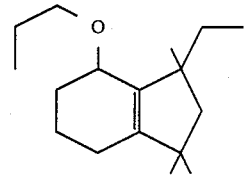

and the compounds having the structures:

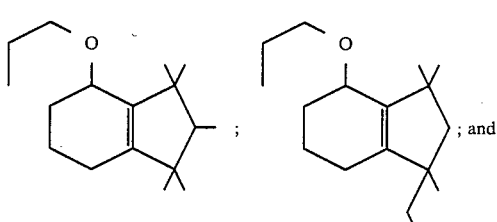

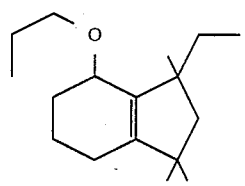

have unexpected, unobvious and advantageous properties when compared with other members of the genus which are ethers, defined according to the structure:

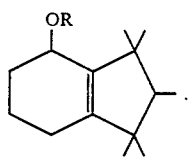

Thus, for example, the compound having the structure:

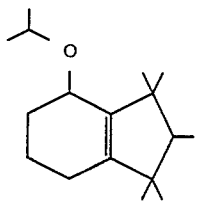

has a "weak woody" aroma profile. Its intensity on a scale of 1 to 10 is "1" as compared to an intensity of "10" for each of the compounds having the structures:

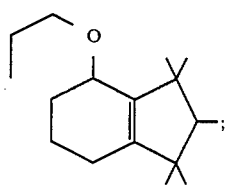

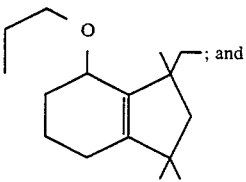

By the same token the compound having the structure:

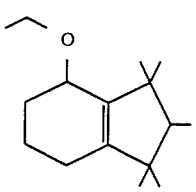

has a weak woody, balsamic aroma and its intensity on a scale of 1 to 10 can be classified as "2.1".

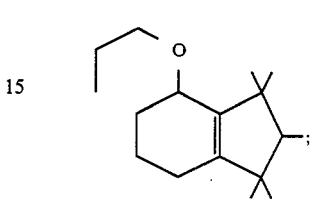

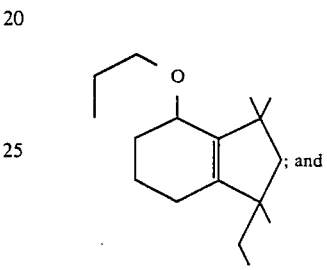

Figure 1:
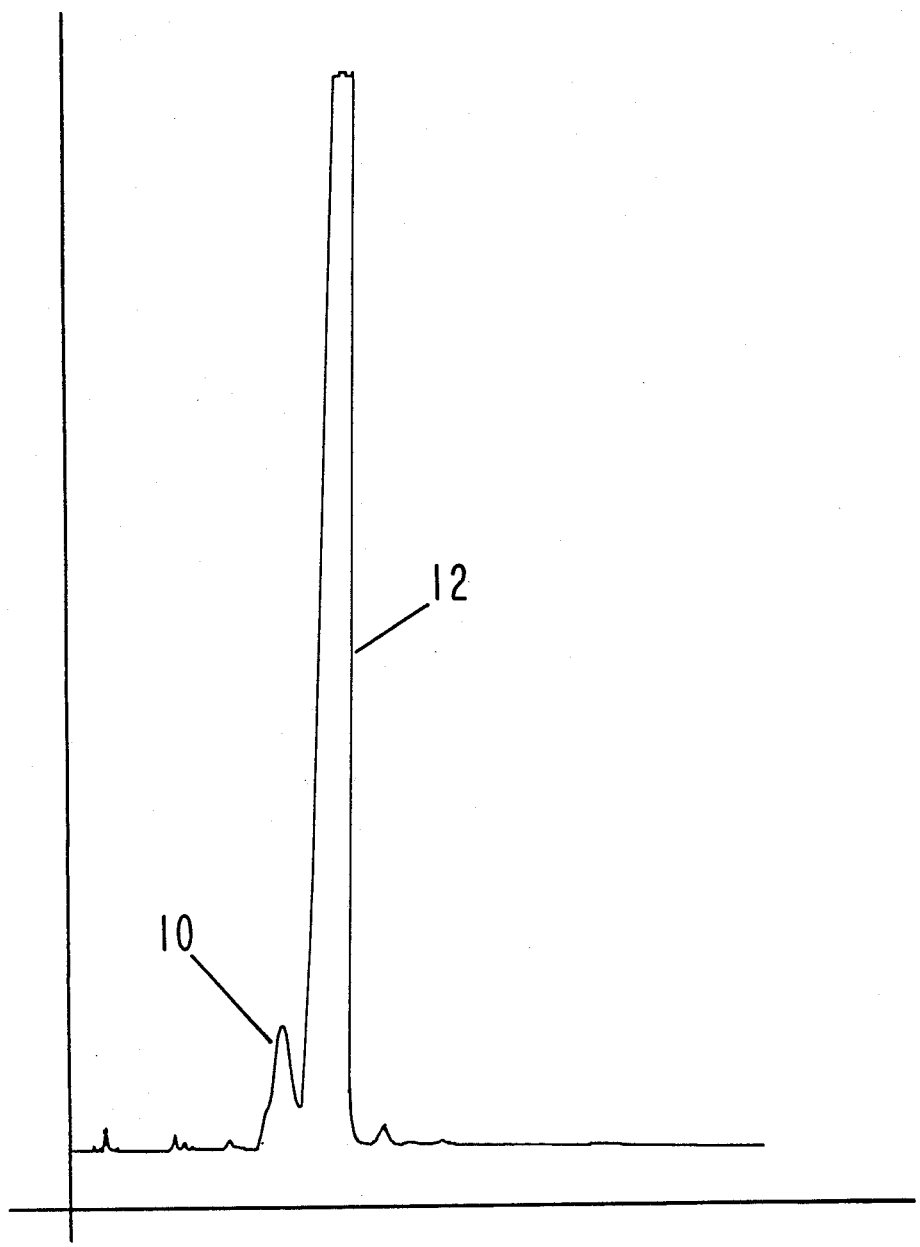
FIG. 1 is the GLC profile for bulked distillation fractions 20-31 of the distillation product of the reaction product of Example I containing the compounds having the structures.
Figure 2:
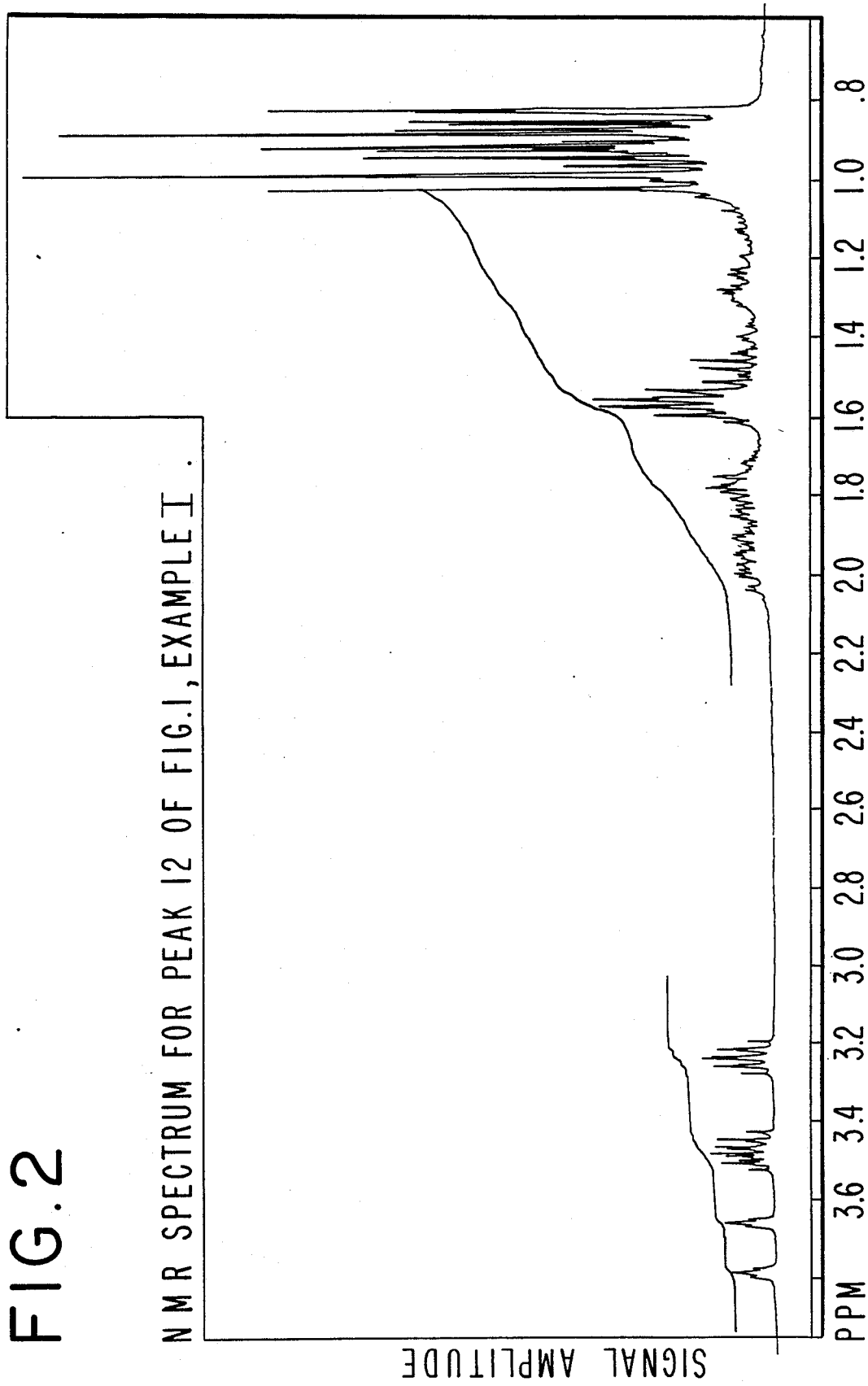

FIG. 2 is the NMR spectrum for the peak indicated by reference numeral 12 of the of the GLC profile of FIG. 1; for the compound having the structure:

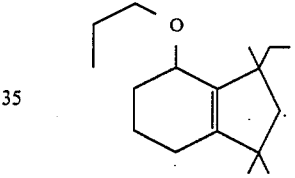

Figure 3:
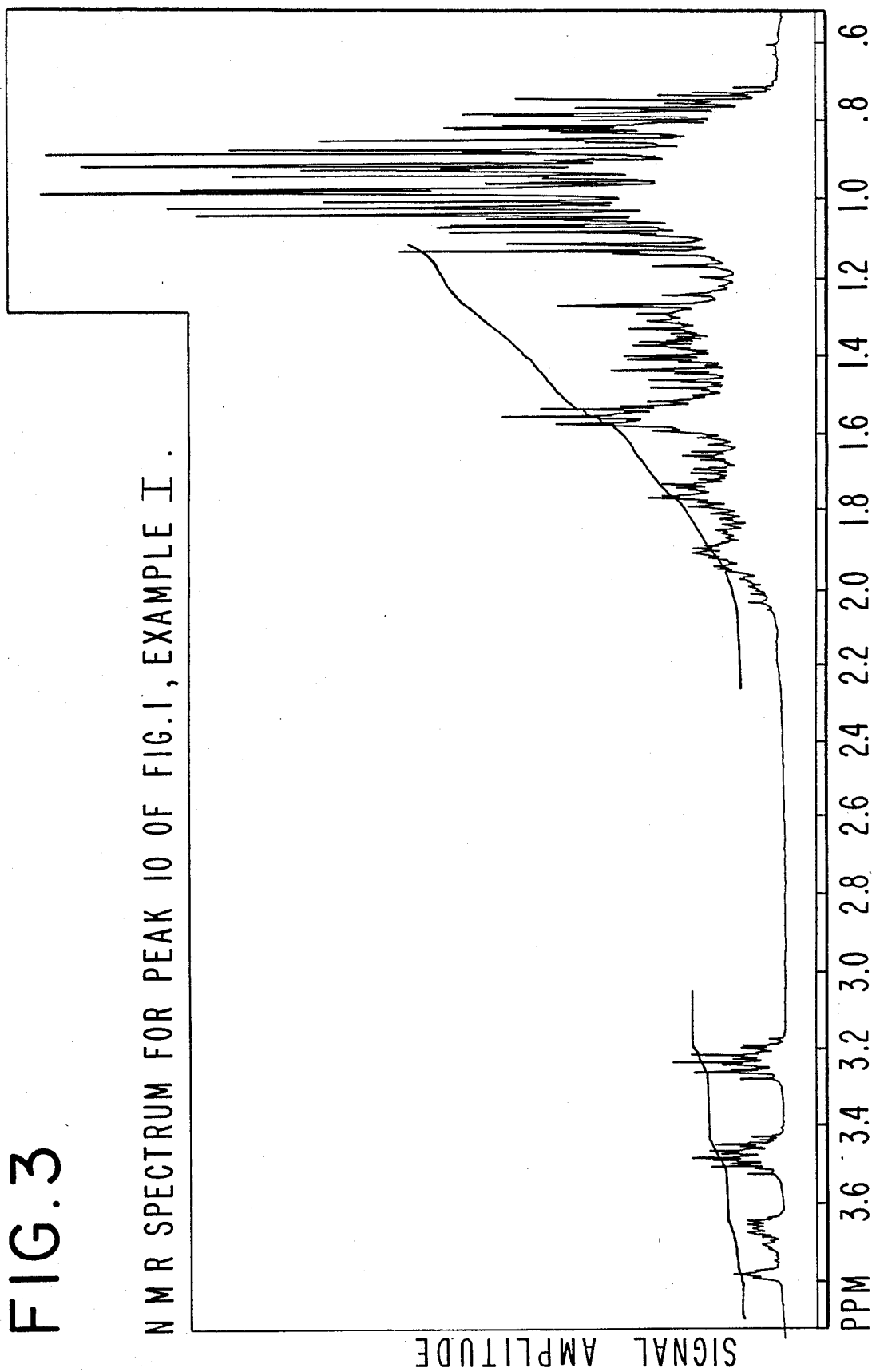

FIG. 3 is the NMR spectrum for the peak indicated by reference numeral 10 of the GLC profile of FIG. 1; for the mixture of compounds having the structures:

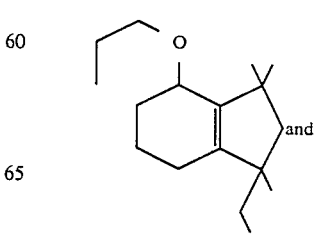

-continued

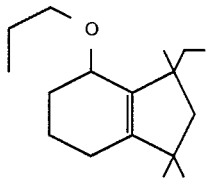

prepared according to Example I.

Figure 4:
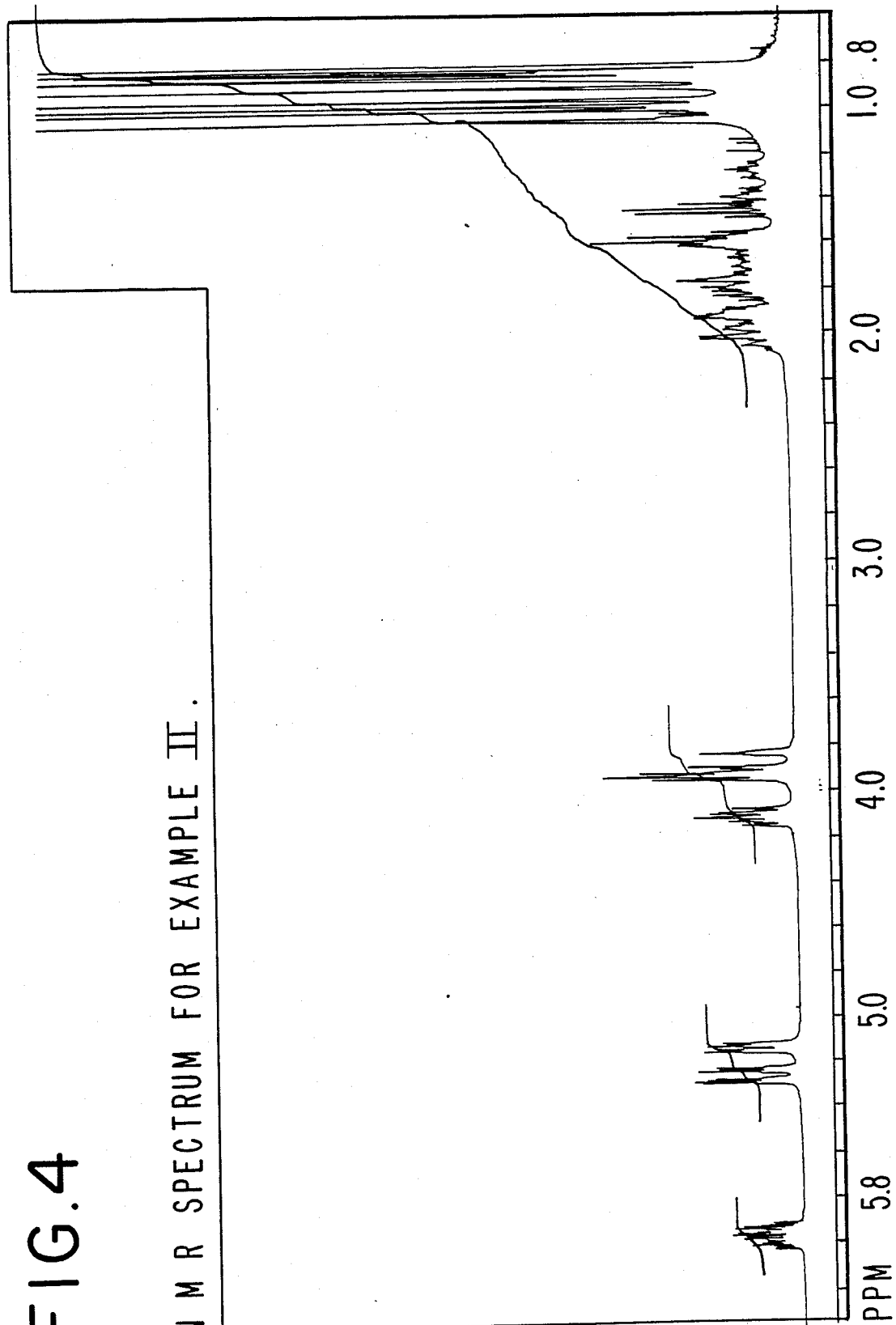

FIG. 4 is the NMR spectrum for the compound having the structure:

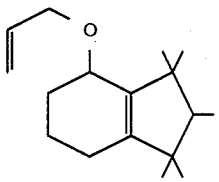

prepared according to Example II.

Figures 5, 6:
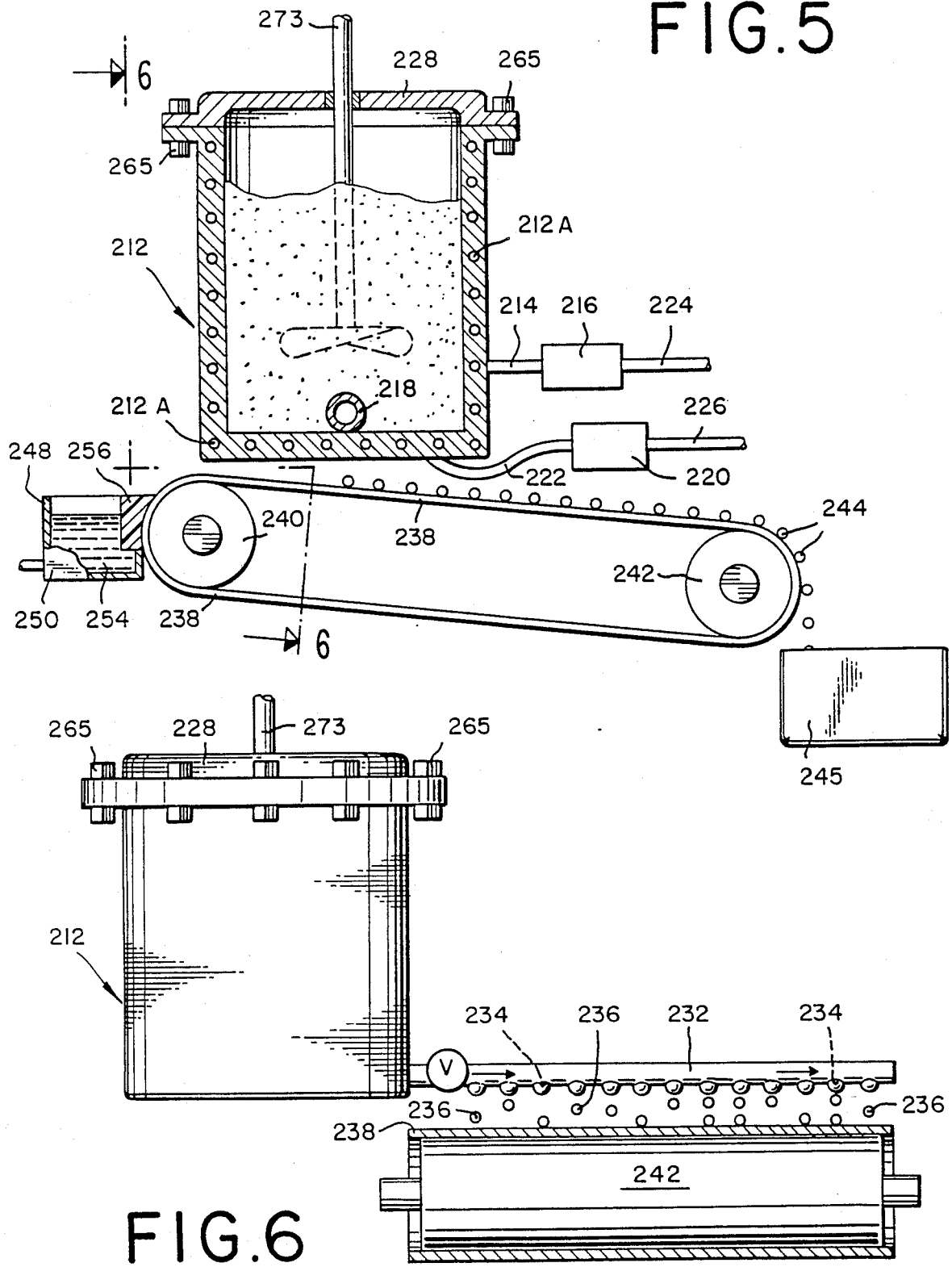

FIG. 5 is a partial side elevation and partial sectional view of an apparatus for forming scented polymers using at least one of the polyalkyl indanyl n-propyl and allyl ethers of our invention.

FIG. 6 is a section taken on line 6—6 of FIG. 5.

DETAILED DESCRIPTION OF THE DRAWINGS

FIG. 1 is the GLC profile for bulked distillation fractions 20-31 of the distillation product of the reaction product of Example I containing the compounds having the structures:

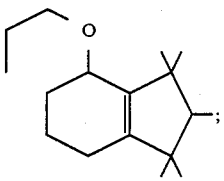

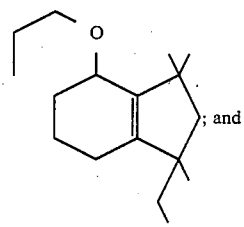
; and

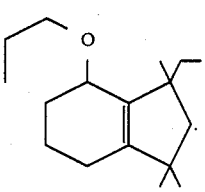

The peak indicated by reference numeral 10 is the peak for the mixture of the compounds having the structures:

and

The peak indicated by reference numeral 12 is for the compound having the structure:

(Conditions: Carbowax column programmed at 160° C. isothermal).

Referring to the drawings in FIGS. 5 and 6, the invention embodied therein comprises a device for forming scented polymer pellets (e.g., polyethylene, polypropylene or mixtures such as polyepsiloncaprolactone and polyethylene or polypropylene or copolymers of polyvinyl acetate and polyethylene or the like) which comprises a vat or container 210 into which a polymer or mixture of polymers admixed with one of the polyalkyl indanyl n-propyl and allyl ethers of our invention is placed.

The container is closed by an air-tight lid 228 clamped to the container by clamps 265. A stirrer 273 traverses the lid or cover 228 in air-tight manner and is rotated in a suitable manner. The surrounding cylinder 212 having heating coils which are supplied with electrical current through cable 214 from a rheostat or control 216 is operated to maintain the temperature inside the container 210 such that the polymer such as polyethylene in the container will be maintained at a molten or liquid state. It has been found advantageous to employ a colorless, odorless polymer such as low density polyethylene with a viscosity ranging between about 180 and about 220 centistokes and having a melting point in the neighborhood of 220° F. The heater 212 is operated to maintain the upper portion of the container 210 within the temperature range of from 250°-350° F. An additional bottom heater 218 is regulated through a control 220 connected thereto through a connecting wire 222 to maintain the lower portion of the container 210 within the temperature range of from 250°-350° F.

In accordance with this aspect of the invention, a polymer such as polyethylene or polypropylene is added to the container 210 and is then heated from 10 to 12 hours whereafter an aroma imparting material containing at least one of the polyalkyl indanyl n-propyl and allyl ethers of our invention or at least one of the polyalkyl indanyl n-propyl and allyl ethers of our invention per se is quickly added to the melt. The mixture containing one of the polyalkyl indanyl n-propyl and allyl ethers of our invention must be compatible with the polymer and forms a homogeneous liquid melt therewith. The heat resisting mixture generally containing from 10 to 40% by weight of the mixture of one of the polyalkyl indanyl n-propyl and allyl ethers of our invention or a mixture thereof is added to container 210; the mixture is stirred for a few minutes, for example, 5-15 minutes, and maintained within the temperature range as indicated previously by the heating coils 212 and 218 respectively. The controls 216 and 220 are connected through cables 224 and 226 through a suitable supply of electric current for supplying the power for heating purposes.

Thereafter, the valve "V" is opened permitting the mass to flow outwardly through a conduit 232 having a multiplicity of orifices 234 adjacent the lower side thereof. The outer end of the conduit 232 is closed so that the liquid polymer and at least one of the polyalkyl indanyl n-propyl and allyl ethers of our invention or mixture containing same will continuously drop or drip through the orifices 234 downwardly from the conduit 232. During this time, the temperature of the polymer and the perfumant mixture containing at least one of the polyalkyl indanyl n-propyl and allyl ethers of our invention in the container 210 is accurately controlled so that a temperature in the range of from 210° F. up to 275° F. will be maintained in the material exiting in the conduit 232. The regulation of the temperature through the control 216 and the control 220 is essential in order to insure temperature balance to provide for the continuous dropping or dripping of the molten polymer and the perfumant containing at least one of the polyalkyl indanyl n-propyl and allyl ethers of our invention through the orifices 234 at a range which will insure the formation of droplets 236 which will fall downwardly onto a moving conveyor belt 238 trained to run between conveyor wheels 240 and 242 beneath the conduit 232. When the droplets 236 fall onto the conveyor belt 238 they form pellets 244 which harden almost instantaneously and fall off the end of the conveyor 238 into a container 246 which is advantageously filled with water or some other suitable liquid to insure the rapid cooling of each of the pellets. The pellets are then collected from the container 246 and packaged for shipment.

A feature of the invention is the provision for the moistening of the conveyor belt 238 to insure the rapid formation of the solid polymer-aromatizing agent containing pellets 244 without sticking to the belt. The belt 238 is advantageously of a material which will not normally stick to a melted polymer, but the moistening means 248 insures a sufficiently cold temperature of the belt surface for the adequate formation of the pellets 244. The moistening means comprises a container 250 which is continuously fed with water 252 to maintain a level 254 for moistening a sponge element 256 which bears against the exterior surface of the belt 238.

THE INVENTION

The present invention provides polyalkyl indanyl n-propyl and allyl ethers defined according to the generic structure:

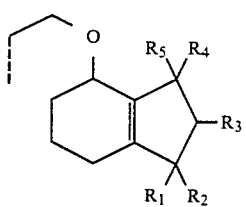

wherein the dashed line represents a carbon-carbon single bond or a carbon-carbon double bond; wherein $R_3$ is methyl or ethyl; and wherein $R_1$, $R_2$, $R_4$ and $R_5$ each represents the same or different methyl or ethyl with the provisos that:
  (i) at least three of $R_1$, $R_2$, $R_4$ and $R_5$ is methyl;
  (ii) when each of $R_1$, $R_2$, $R_4$ and $R_5$ is methyl, then $R_3$ is methyl; and
  (iii) when the dashed line is a carbon-carbon double bond then $R_1$, $R_2$, $R_3$, $R_4$ and $R_5$ are each methyl.

The polyalkyl indanyl n-propyl and allyl ethers of our invention have utilities in perfumery; that is, in augmenting or enhancing the aroma of perfume compositions, colognes and perfumed articles including but not limited to solid or liquid anionic, cationic, nonionic or zwitterionic detergents, fabric softener compositions, fabric softener articles, cosmetic powders and hair preparations and perfumed polymers. The polyalkyl indanyl n-propyl and allyl ethers of our invention are prepared by first reacting a cyclic hexenol derivative defined according to the structure:

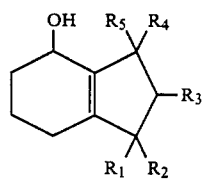

with an alkali metal hydride having the formula:

MH according to the reaction:

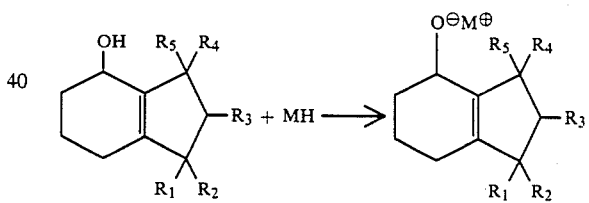

thereby forming the compounds defined according to the structure:

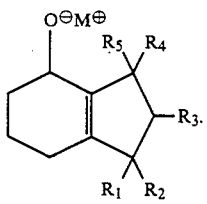

The compound having the structure:

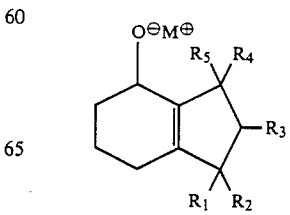

which is intended to include mixtures of compounds having the structures:

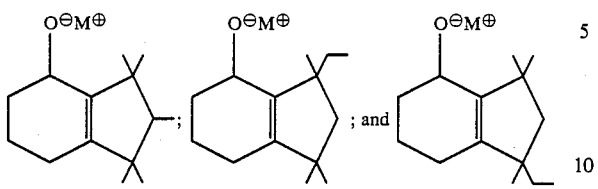

is then reacted with allyl bromide or n-propyl bromide defined according to the generic structure:

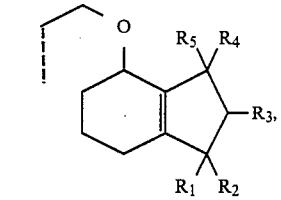

wherein the dashed line is a carbon-carbon single bond or a carbon-carbon double bond according to the reaction:

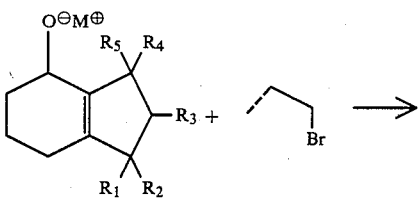

thereby forming a member of the genus having the structure:

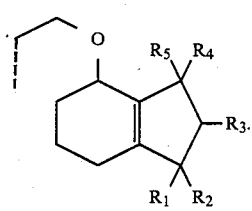

The compounds defined according to the generic structure:

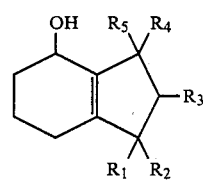

may be prepared according to the techniques as set forth in U.S. Letters Pat. No. 3,636,165 the specification of which is incorporated herein by reference.

The reactions for production of the polyalkyl indanyl n-propyl and allyl ethers of our invention defined according to the structure:

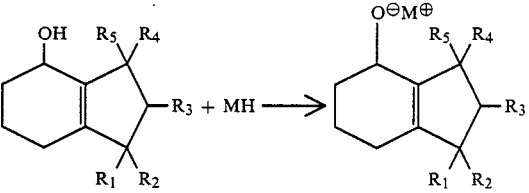

namely, the reactions:

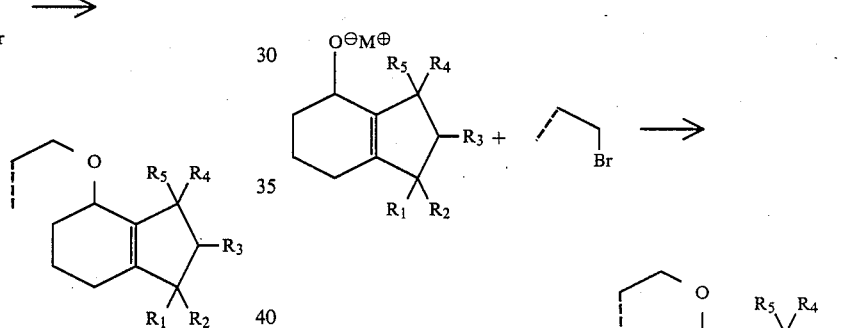

and

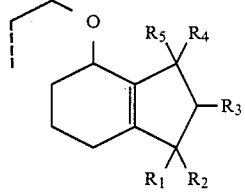

may be carried out in accordance with conditions as set forth in said U.S. Letters Pat. No. 3,636,165 issued on January 18, 1972.

Conditions for such a reaction sequence are also set forth in U.S. Letters Pat. No. 4,782,192 the specification for which is incorporated herein by reference.

Thus, compounds having the generic structure:

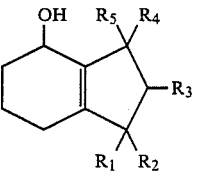

are first reacted with an alkali metal hydride such as sodium or potassium hydride or in the alternative with n-butyl lithium to form the resulting metal salt defined according to the generic structure:

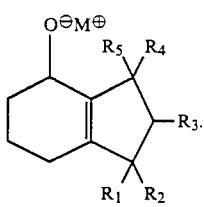

The reaction is preferably carried out in an inert solvent such as diethyl ether or tetrahydrofuran in admixture with toluene at reflux temperatures, e.g., the boiling point of the solvent composition at atmospheric pressure.

At the end of the reaction to form the salt defined according to the generic structure:

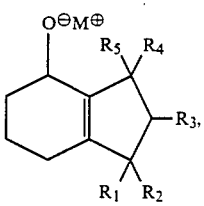

the said salt is then reacted with an allyl halide or a propyl halide defined according to the generic structure:

that is, one of the compounds having the structures:

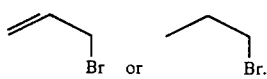

The reaction, to wit:

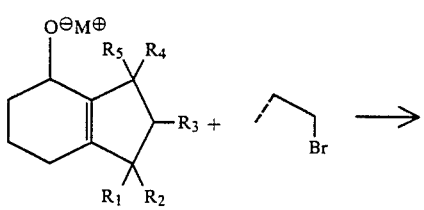

is also carried out at reflux conditions in the presence of the solvent that was previously used in the reaction to form the salt having the structure:

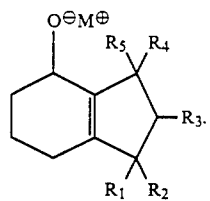

Immediately upon the cessation of the reaction and after the solvent is stripped, the reaction mass is washed in order to purify it by means of ordinary "work up" techniques; and then the reaction mass is distilled to yield the odor acceptable fraction or fractions for use for their respective organoleptic properties.

Examples of the polyalkyl indanyl n-propyl and allyl ethers of our invention produced according to the processes of our invention and their organoleptic properties are set forth in the following Table I:

TABLE I

| Structure of The Polyalkyl Indanyl n-Propyl And Allyl Ethers Of Our Invention | Perfumery Evaluation |
|---|---|
| Mixture of compounds defined according to the structures: 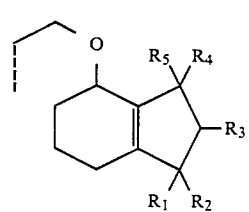 and <br> prepared according to Example I, bulked distillation fractions 6–12. | A musky, cigar box-like, amber, woody, patchouli and camphoraceous aroma with woody and winey topnotes. |
| Mixture of compounds having the structures: 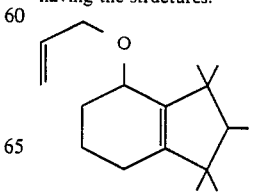 + | A woody aroma with balsamic topnotes. |

TABLE I-continued

Structure of The
Polyalkyl Indanyl n-Propyl
And Allyl Ethers Of Our
Invention          Perfumery Evaluation

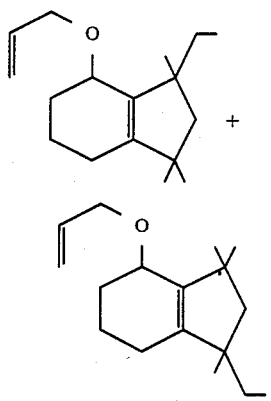

prepared according
to Example II.

One or more of the polyalkyl indanyl n-propyl and allyl ethers of our invention and one or more auxiliary perfume ingredients including, alcohols, aldehydes, ketones, ethers other than the polyalkyl indanyl n-propyl and allyl ethers of our invention, esters, terpenic hydrocarbons, nitriles, lactones, natural essential oils and synthetic essential oils, may be admixed so that the combined odors of the individual components produce a pleasant and desired fragrance, particularly in the musk, amber and patchouli fragrances.

Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh smelling materials.

In perfume compositions, it is the individual components which contribute to their particular olfactory characteristics, however the over-all sensory effect of the perfume composition will be at least the sum total of the effects of each of the ingredients. Thus, one or more of the polyalkyl indanyl n-propyl and allyl ethers of our invention can be used to alter, modify or enhance the aroma characteristics of a perfume composition, for example, by utilizing or moderating the olfactory reaction contributed by another ingredient in the composition.

The amount of one or more of the polyalkyl indanyl n-propyl and allyl ethers of our invention which will be effective in perfume compositions as well as in perfumed articles and colognes depends on many factors, including the other ingredients, their amounts and the effects which are desired. It has been found that perfume compositions containing as little 0.01% of one or more of polyalkyl indanyl n-propyl and allyl ethers of our invention or even less (e.g., 0.005%) can be used to augment or enhance or impart musky, cigar box-like, amber, woody, patchouli and camphoraceous aromas with woody, winey and balsamic topnotes to soaps, cosmetics, solid or liquid anionic, cationic, nonionic or zwitterionic detergents, powders, fabric softeners, drier added fabric softener articles, hair conditioners and colognes. The amount employed can range up to 70% of the fragrance components and will depend upon considerations of cost, nature of the end product, the effect desired on the finished product and the particular fragrance sought.

The polyalkyl indanyl n-propyl and allyl ethers of our invention are useful (taken alone or taken further together with other ingredients in perfume compositions) as (an) olfactory component(s) in detergents and soaps, space odorants and deodorants, perfumes, colognes, toilet water, bath preparations, such as lacquers, brilliantines, pomades and shampoos; cosmetic preparations, such as creams, deodorants, hand lotions and sun screens; powders, such as talcs, dusting powders, face powders and the like. When used as (an) olfactory component(s) as little as 1% of the polyalkyl indanyl n-propyl and allyl ethers of our invention will suffice to impart intense and long-lasting musky, cigar box-like, amber, woody, patchouli and camphoraceous aromas with woody, winey nd balsamic topnotes to various formulations such as patchouli formulations. Although generally, no more than 60% of the polyalkyl indanyl n-propyl and allyl ethers of our invention, based on the ultimate end product, is required in the perfume composition, amounts of polyalkyl indanyl n-propyl and allyl ethers of our invention of up to 95% may be used in such perfume compositions.

When used in perfumed articles such as anionic, cationic, nonionic or zwitterionic detergents, or dryer-added fabric softener articles, cosmetic powders or deodorant compositions, from 0.1% up to 5.0% of the polyalkyl indanyl n-propyl and allyl ethers of our invention based on the over-all perfumed article weight may be used in the perfumed articles to impart intense and long-lasting, musky, cigar box-like, amber, woody, patchouli and camphoraceous aromas with woody, winey and balsamic topnotes.

In addition, the perfume compositions of our invention can contain a vehicle or carrier for the polyalkyl indanyl n-propyl and allyl ethers of our invention alone or with other ingredients. The vehicle can be a liquid such as an alcohol, such as ethanol, a glycol such as propylene glycol or the like.

The carrier can be an absorbent solid such as a gum (e.g., xanthan gum or gum arabic) or components for encapsulating the composition as by coacervation in gelatin or by forming a polymeric shell around a liquid perfume center by means of the use of, for example, a ureaformaldehyde prepolymer.

The following Examples I and II set forth processes for preparing the polyalkyl indanyl n-propyl and allyl ethers of our invention. Example III, et seq. set forth methods for using the polyalkyl indanyl n-propyl and allyl ethers of our invention for their organoleptic properties.

Unless otherwise indicated, all parts and percentages are by weight.

EXAMPLE I

Preparation of
N-Propyl-4,5,6,7-Tetrahydro-1,1,2,3,3-Pentamethyl-4-Indanyl Ether and Isomers Reactions:

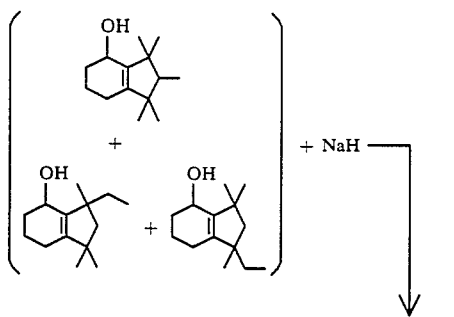

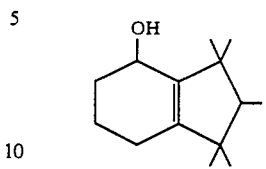

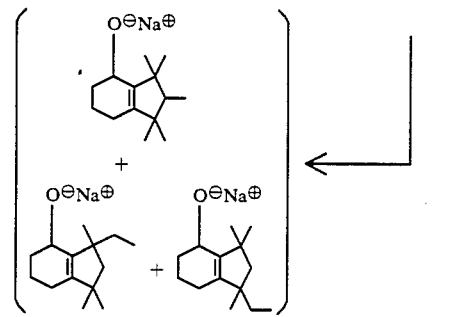

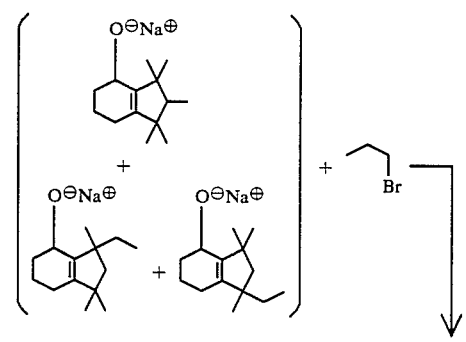

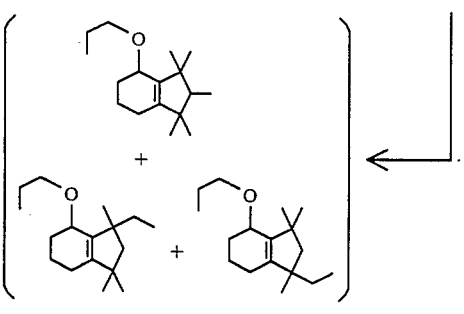

A solution of 1040 grams of 4,5,6,7-tetrahydro-1,1,2,3,3-pentamethyl-4-indanyl and isomers thereof having the structures:

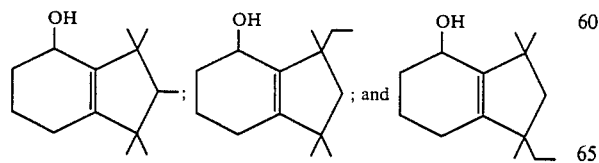

prepared according to Example I(c) of U.S. Pat. No. 3,636,165 the specification for which is incorporated by reference herein (with the mole ratio of the compound having the structure:

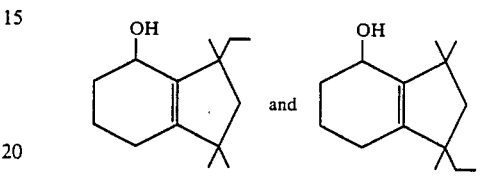

to the mixture of compounds having the structures:

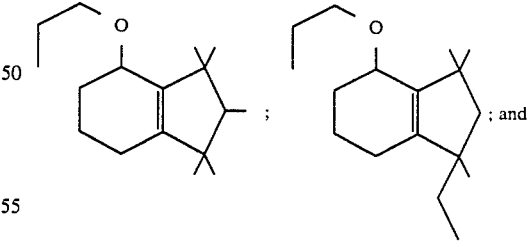

being 10:1) in 1500 ml of tetrahydrofuran is added at reflux over a four hour period to a stirred slurry of 60% sodium hydride (210 grams) in 2000 ml of tetrahydrofuran and 1000 ml of toluene. Hydrogen gas is evolved. The reaction mass is heated at reflux for an additional two hour period until hydrogen evolution ceases. 1-Bromo propane (680 grams) is then added at reflux over a period of two hours. The reaction mass is heated at reflux for an additional one hour. The solvent (tetrahydrofuran and toluene) is distilled off at atmospheric pressure to a pot temperature of 95° C. The reaction mass is cooled to 40° C. 3000 ml of water is added. The reaction mass is stirred for 30 minutes.

The lower (aqueous) phase is split-off. The upper (organic) phase is washed with 2000 ml of 10% sodium hydroxide solution and then distilled. Fractional distillation afforded 920 grams of the mixture of compounds having the structures:

with the mole ratio of the compound having the structure:

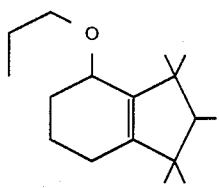

to the mixture of compounds having the structures:

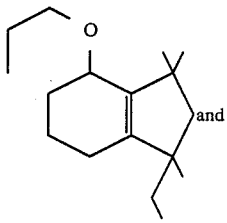

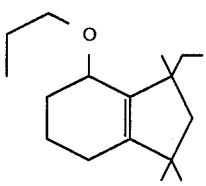

being 10:1. The boiling point is 110° C. at 1 mm/Hg. pressure.

More specifically, the distillation is carried out using a packed column yielding the following fractions:

| Fraction No. | Vapor Temp. (°C.) | Liquid Temp. (°C.) | Vacuum mm/Hg. Pressure | Reflux Ratio |
| --- | --- | --- | --- | --- |
| 1 | 23/88 | 23/112 | 50/8 | 100 |
| 2 | 88 | 112 | 7 | 100 |
| 3 | 92 | 115 | 7 | 100 |
| 4 | 92 | 118 | 7 | 100 |
| 5 | 92 | 122 | 4 | 100 |
| 6 | 96 | 125 | 4 | 100 |
| 7 | 96 | 128 | 4 | 1:1 |
| 8 | 96 | 128 | 4 | 1:1 |
| 9 | 100 | 128 | 4 | 1:7 |
| 10 | 104 | 130 | 2 | 1:1 |
| 11 | 110 | 130 | 1 | 1:1 |
| 12 | 110 | 130 | 1 | 1:1 |
| 13 | 109 | 135 | 1 | 1:1 |
| 14 | 108 | 136 | 1 | 1:1 |
| 15 | 100 | 138 | 1 | 1:1 |
| 16 | 108 | 136 | 1 | 1:1 |
| 17 | 110 | 136 | 1 | 1:1 |
| 18 | 110 | 137 | 1 | 100 |
| 19 | 110 | 137 | 1 | 100 |
| 20 | 110 | 137 | 1 | 100 |
| 21 | 110 | 138 | 1 | 100 |
| 22 | 110 | 138 | 1 | 100 |
| 23 | 110 | 138 | 1 | 100 |
| 24 | 110 | 138 | 1 | 100 |
| 25 | 110 | 138 | 1 | 100 |
| 26 | 108 | 138 | 1 | 100 |
| 27 | 108 | 140 | 1 | 100 |
| 28 | 108 | 140 | 1 | 100 |
| 29 | 108 | 145 | 1 | 100 |
| 30 | 108 | 150 | 1 | 100 |
| 31 | 108 | 160 | 1 | 100 |
| 32 | 108 | 170 | 1 | 100 |
| 33 | 108 | 185 | 1 | 100 |

FIG. 1 is the GLC profile for bulked distillation fractions 20–31 of the foregoing distillation (Conditions: Carbowax column programmed at 160° C. isothermal). The peak indicated by reference numeral 10 is the peak for the mixture of compounds having the structures:

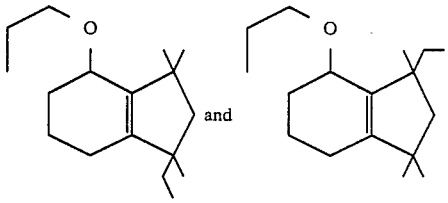

The peak indicated by reference numeral 12 is the peak for the compound having the structure:

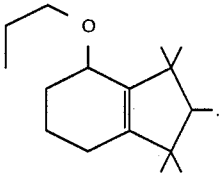

FIG. 2 is the NMR spectrum for the compound having the structure:

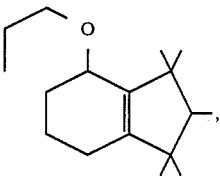

of the peak indicated by reference numeral 12 of the GLC profile of FIG. 1.

FIG. 3 is the NMR specturm for the mixture of compounds having the structures:

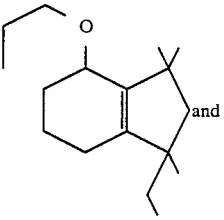

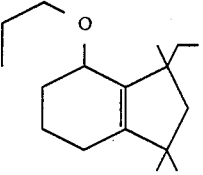

which is from peak 10 of the GLC profile of FIG. 1.

Bulk distillation fractions 6–12 of the foregoing distillation has a musky, cigar box-like, amber, woody, patchouli and camphoraceous aroma with woody and winey topnotes.

EXAMPLE II

Production of Allyl-4,5,6,7-Tetrahydro-1,1,2,3,3-Pentamethyl-4-Indanyl Ether and Isomers Reactions:

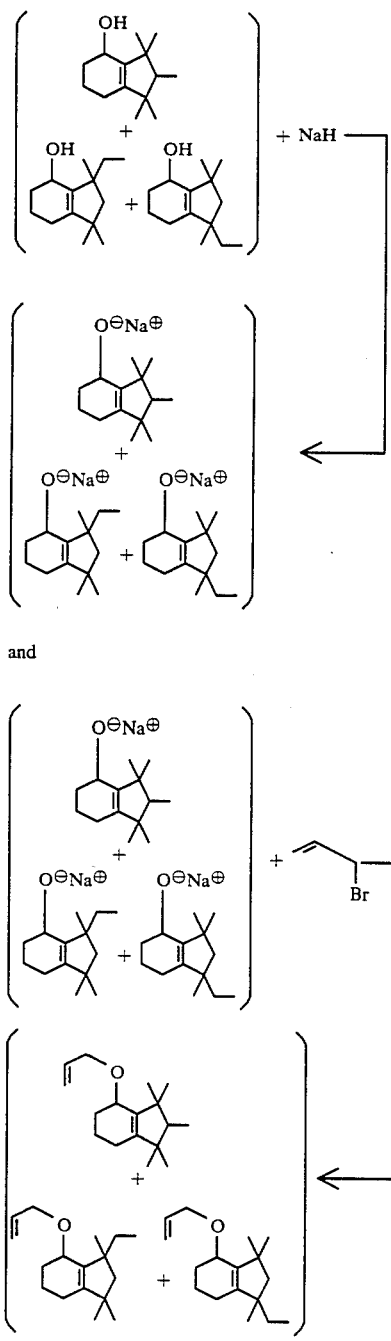

and

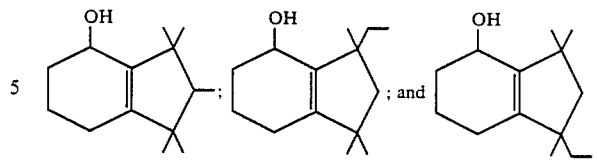

prepared according to Example I(c) of U.S. Pat. No. 3,636,165 is added to the reaction mass over one hour with sufficient cooling so that the temperature does not rise substantially above 50°–60° C. The reaction mass is stirred so as to produce a complete evolution of hydrogen.

After evolution of hydrogen ceases, 7.6 grams of allyl bromide is added with cooling to maintain the temperature at 50° C. for a period of two hours. Then, 40 ml of water and 10 ml of toluene are added. The organic layer is separated and the water layer is extracted with 10 ml of toluene. The toluene extract is combined with the organic phase and the mixture is washed once with 10 ml of 5% aqueous hydrochloric acid and twice with 10 ml of water. The solvent is stripped off to provide a crude ether product weighing 12.0 grams.

The crude product is vacuum-distilled yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 23/30 | 23/110 | 100/20 | 1.00 |
| 2 | 100 | 120 | 10 | 1.00 |
| 3 | 100 | 120 | 10 | 4:0 |
| 4 | 100 | 134 | 9 | 4:1 |
| 5 | 110 | 140 | 9 | 4:1 |
| 6 | 118 | 145 | 9 | 4:1 |
| 7 | 122 | 148 | 9 | 4:1 |
| 8 | 135 | 148 | 9 | 4:1 |
| 9 | 100 | 142 | 3 | 9:1 |
| 10 | 100 | 142 | 3 | 1:1 |
| 11 | 100 | 142 | 3 | 1:1 |
| 12 | 100 | 142 | 3 | 1:1 |
| 13 | 104 | 145 | 3 | 1:1 |
| 14 | 106 | 140 | 3 | 1:1 |
| 15 | 108 | 155 | 3 | 1:1 |
| 16 | 95 | 165 | 3 | 1:1 |
| 17 | 90 | 195 | 3 | 1:1 |

The resulting product is a mixture of compounds having the structures:

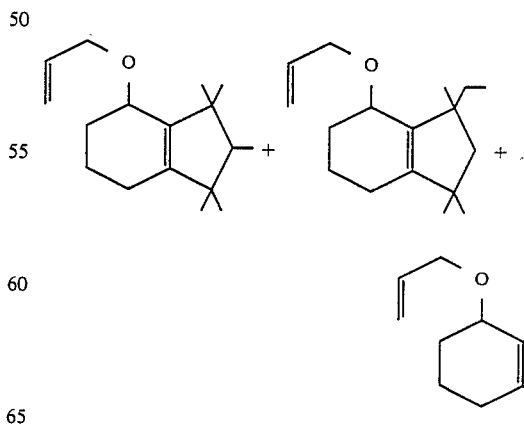

Into a 100 ml reaction flask equipped with stirrer, thermometer, reflux condenser and heater and nitrogen purge are introduced 2.7 grams of 52.5% sodium hydride and 20.0 grams of dimethyl formamide. While stirring, a solution of 12.0 grams of the mixture of compounds having the structures:

FIG. 4 is the NMR spectrum for the mixture of compounds having the structures:

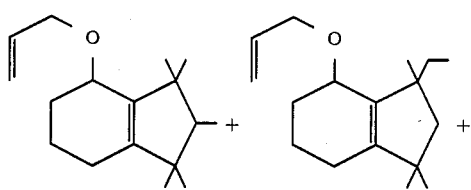

The mixture of compounds having the structures:

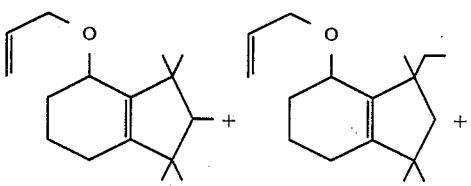

has a woody aroma with balsamic topnotes.

EXAMPLE III

Woody fragrance formulation prepared using products prepared according to Examples I and/or II:

| Ingredients | Parts by Weight | | |
|---|---|---|---|
| | III(A) | III(B) | III(C) |
| Vetiver oil | 40 | 40 | 40 |
| Ethyl alcohol | 60 | 60 | 60 |
| Sandalwood oil E.I. | 100 | 100 | 100 |
| Rose geranium oil | 200 | 200 | 200 |
| Civetone | 25 | 25 | 25 |
| Benzyl isoeugenol | 100 | 100 | 100 |
| Coumarin | 100 | 100 | 100 |
| Heliotropin | 50 | 50 | 50 |
| Bois de rose oil | 200 | 200 | 200 |
| Benzoin resin | 100 | 100 | 100 |
| Mixture of compounds having the structures: | | | |

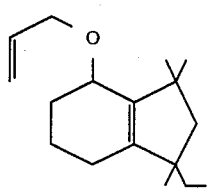

| | Parts by Weight | | |
|---|---|---|---|
| Ingredients | III(A) | III(B) | III(C) |

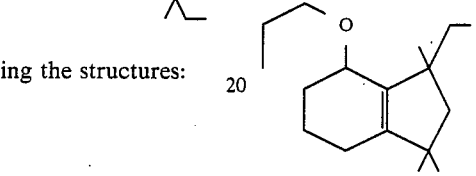

and

| | 20 | 0 | 0 | prepared according to Example I, bulked fractions 6–12. Mixture of compounds having the structures:

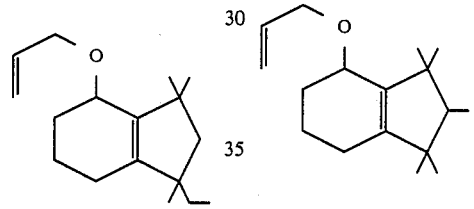

| + | 0 | 20 | 0 | prepared according to Example II. 50:50 Mixture of compounds having the structures:

-continued

| Ingredients | Parts by Weight | | |
|---|---|---|---|
| | III(A) | III(B) | III(C) |
| 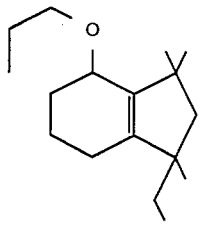 and 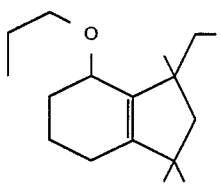 and compounds having the structures: 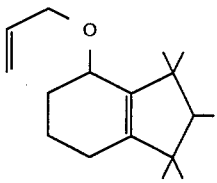 + 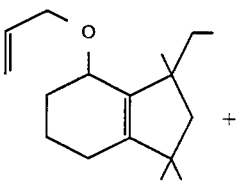 prepared, respectively, according to Example I and II. | 0 | 0 | 20 |

The perfume composition of Example III(A) has a woody, balsamic aroma with woody and winey topnotes and musky, cigar box-like, amber, woody, patchouli and camphoraceous undertones.

The perfume composition of Example III(B) has a woody, balsamic aroma with balsamic topnotes and intense mahogany-like undertones.

The perfume composition of Example III(C) has a woody, balsamic aroma with woody, winey and balsamic topnotes and musky, cigar box-like, amber, woody, patchouli and camphoraceous undertones.

EXAMPLE IV

Preparation of Cosmetic Powder Composition

Cosmetic powder compositions are prepared by mixing in a ball mill 100 grams of talcum powder with 0.25 grams of each of the substances set forth in Table II below. Each of the cosmetic powder compositions has an excellent aroma as described in Table II below.

TABLE II

| Substance | Aroma Description |
|---|---|
| Mixture of compounds having the structures: 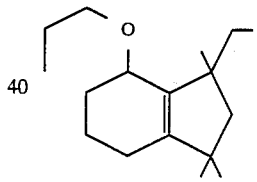 and 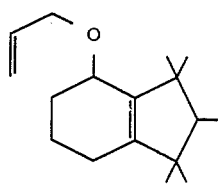 prepared according to Example I, (bulked fractions 6–12). | A musky, cigar box-like, amber, woody, patchouli and camphoraceous aroma with woody and winey topnotes. |
| Mixture of compounds having the structures: 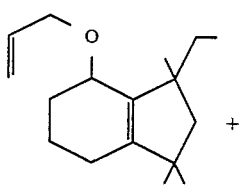 + | A woody aroma with balsamic topnotes. |

TABLE II-continued

| Substance | Aroma Description |
|---|---|
| [structure] prepared according to Example II. | |
| Perfume composition of Example III(A). | A woody, balsamic aroma with woody and winey topnotes and musky, cigar box-like, amber, woody, patchouli and camphoraceous undertones. |
| Perfume composition Example III(B). | A woody, balsamic aroma with balsamic topnotes and intense mahogany-like undertones. |
| Perfume composition of Example III(C). | A woody, balsamic aroma with woody, winey and balsamic topnotes and musky, cigar box-like, amber, woody, patchouli and camphoraceous undertones. |

EXAMPLE V

Perfumed Liquid Detergents

Concentrated liquid detergents (lysine salt of n-dodecylbenzene sulfonic acid as more specifically described in U.S. Pat. No. 3,948,818 issued April 6, 1976 incorporated by reference herein) with aroma nuances as set forth in Table II of Example IV, are prepared containing 0.10%, 0.15%, 0.20%, 0.25%, 0.30% and 0.35% of the substance set forth in Table II of Example IV. They are prepared by adding and homogeneously mixing the appropriate quantity of substance set forth in Table II of Example IV in the liquid detergent. The detergents all possess excellent aromas as set forth in Table II of Example IV, the intensity increasing with greater concentrations of substance as set forth in Table II of Example IV.

EXAMPLE VI

Preparation of Colognes and Handkerchief Perfumes

Compositions as set forth in Table II of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definite fragrances as set forth in Table II of Example IV are imparted to the colognes and to the handkerchief perfumes at all levels indicated.

EXAMPLE VII

Preparation of Soap Compositions

One hundred grams of soap chips (per sample)- (IVORY ® produced by the Procter & Gamble Company of Cincinnati, Ohio), are each mixed with one gram samples of substances as set forth in Table II of Example IV until homogeneous compositions are obtained. In each of the cases, the homogeneous compositions are heated under 8 atmospheres, pressure at 180° C. for a period of three hours and the resulting liquids are placed into soap molds. The resulting soap cakes, on cooling manifest aromas as set forth in Table II of Example IV.

EXAMPLE VIII

Preparation of Solid Detergent Compositions

Detergents are prepared using the following ingredients according to Example I of Canadian Pat. No. 1,007,948 (incorporated by reference herein):

| Ingredient | Percent by Weight |
|---|---|
| NEODOL ® 45-11 (a $C_{14}$—$C_{15}$ alcohol ethoxylated with 11 moles of ethylene oxide | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example IV. Each of the detergent samples has an excellent aroma as indicated in Table II of Example IV.

EXAMPLE IX

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and the perfuming material are as follows:
 1. A water "dissolvable" paper ("Dissolvo Paper");
 2. Adogen 448 (m.p. about 140° F.) as the substrate coating; and
 3. An outer coating having the following formulation (m.p. about 150° F.):
  57% $C_{20-22}$ HAPS
  22% isopropyl alcohol
  20% antistatic agent
  1% of one of the substances as set forth in Table II of Example IV.

Fabric softening compositions prepared according to Example I at column 15 of U.S. Pat. No. 3,632,396 having aroma characteristics as set forth in Table II of Example IV, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener non-woven fabrics and these aroma characteristics are described in Table II of Example IV, supra.

EXAMPLE X

Hair Spray Formulations

The following hair spray formulation is prepared by first dissolving PVP/VA E-735 copolymer manufactured by the GAF Corporation of 140 West 51st Street, New York, New York in 91.62 grams of 95% food grade ethanol. 8.0 Grams of the polymer is dissolved in the alcohol. The following ingredients are added to the PVP/VA alcoholic solution:

|  | Weight Percent |
|---|---|
| Dioctyl sebacate | 0.05 |
| Benzyl alcohol | 0.10 |
| Dow Corning 473 fluid prepared by the Dow Corning Corporation | 0.10 |
| TWEEN ® 20 surfactant (prepared by ICI America Corporation) | 0.03 |
| One of the perfumery substances as set forth in Table II of Example IV. | 0.10 |

The perfuming substances as set forth in Table II of Example IV add aroma characteristics as set forth in Table II of Example IV which are rather intense and aesthetically pleasing to the users of the soft-feel, good-hold pump hair sprays.

EXAMPLE XI

Conditioning Shampoos

A Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation)(1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

GAFQUAT® 755N polymer (manufactured by GAF Corporation of 140 West 51st Street, New York)(5.0 weight percent) is admixed with 0.1 weight percent sodium sulfite and 1.4 weight percent polyethylene glycol 6000 distearate produced by Armak Corporation. This material is "Composition B".

The resulting "Composition A" and "Composition B" are then mixed in a 50:50 weight ratio of A:B and cooled to 45° C. and 0.3 weight percent of perfuming substance as set forth in Table II of Example IV add to the mixture. The resulting mixture is cooled to 40° C. and blending is carried out for an additional one hour in each case. At the end of this blending period, the resulting material has a pleasant fragrance as indicated in Table II of Example IV.

EXAMPLE XII

Scented polyethylene pellets having a pronounced scent as set forth in Table II of Example IV are prepared as follows:

75 Pounds of polyethylene of a melting point of about 200° F. are heated to about 230° F. in a container of the kind illustrated in FIGS. 5 and 6. 25 Pounds of each of the perfumery materials of Table II of Example IV, supra, are then added quickly to the liquified polyethylene. The lid 228 is put in place and the agitating means 273 are actuated. The temperature is maintained at about 225° F. and the mixing is then continued for about 5–15 minutes. The valve "V" is then opened to allow flow of the molten polyethylene enriched with each of the aroma containing materials to exit through the orifices 234. The liquid falling through the orifices 234 solidify almost instantaneously upon impact with the moving, cooled conveyor 238. Solid polyethylene beads or pellets 244 having pronounced aromas as set forth in Table II of Example IV, supra, are then formed. Analysis demonstrates that the pellets contain about 25% of each of the perfume substances of Table II of Example IV so that almost no losses of the scenting substance occur. These pellets may be called master pellets.

50 Pounds of the scent-containing master pellets are then added to 1,000 pounds of unscented polyethylene powder and the mass is heated to the liquid state. The liquid is molded into thin sheets or films. The sheets or films have a pronounced aroma as set forth in Table II of Example IV, supra. The sheets are also fabricated into garbage bags which have aromas as set forth in Table II of Example IV, supra.

What is claimed is:

1. A mixture of compounds defined according to the structures:

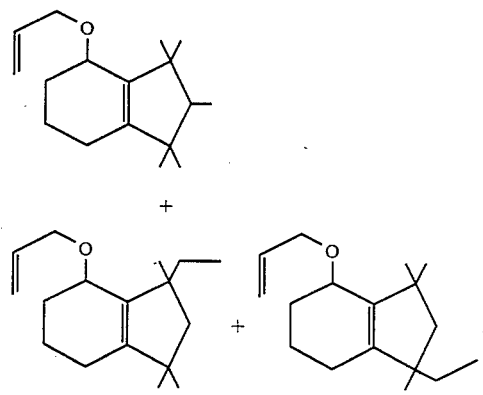

2. A mixture of compounds defined according to the structures:

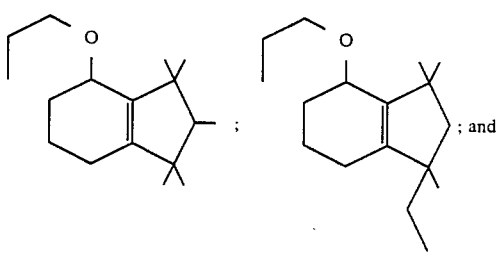

; and

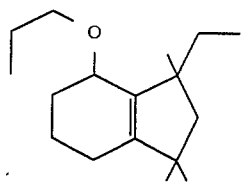

3. A process for augmenting or enhancing the aroma of a perfume composition, cologne or perfumed article comprising the step of intimately admixing with a perfume base, a cologne base or a perfumed article base, an aroma augmenting or enhancing quantity of the composition of matter defined according to claim 1.

4. A process for augmenting or enhancing the aroma of a perfume composition, cologne or perfumed article comprising the step of intimately admixing with a perfume base, a cologne base or a perfumed article base, an aroma augmenting or enhancing quantity of the composition of matter defined according to claim 2.

* * * * *